(12) United States Patent
Woodmansee et al.

(10) Patent No.: US 10,272,105 B2
(45) Date of Patent: Apr. 30, 2019

(54) PLANT MEDIUM INCLUDING AN OXYGEN-ENABLED COMPOSITION

(71) Applicants: Caree L. Woodmansee, Marshall, TX (US); Robert A Woodmansee, Plano, TX (US); John W Woodmansee, Jr., Frisco, TX (US); William E. Harmon, Russellville, AR (US)

(72) Inventors: Caree L. Woodmansee, Marshall, TX (US); Robert A Woodmansee, Plano, TX (US); John W Woodmansee, Jr., Frisco, TX (US); William E. Harmon, Russellville, AR (US)

(73) Assignee: HEMOTEK, LLC, Plano, TX (US)

( * ) Notice: Subject to any disclaimer, the term of this patent is extended or adjusted under 35 U.S.C. 154(b) by 0 days.

(21) Appl. No.: 16/152,977

(22) Filed: Oct. 5, 2018

(65) Prior Publication Data

US 2019/0038665 A1 Feb. 7, 2019

Related U.S. Application Data

(63) Continuation-in-part of application No. 15/983,602, filed on May 18, 2018, now Pat. No. 10,137,146,
(Continued)

(51) Int. Cl.
*A61K 33/08* (2006.01)
*A61K 47/69* (2017.01)
(Continued)

(52) U.S. Cl.
CPC .......... *A61K 33/08* (2013.01); *A61K 9/0019* (2013.01); *A61K 9/0026* (2013.01);
(Continued)

(58) Field of Classification Search
None
See application file for complete search history.

(56) References Cited

U.S. PATENT DOCUMENTS 6,500,539 B1 * 12/2002 Chen ................... A61L 15/26
428/364
9,682,103 B1 * 6/2017 Bruce ................... A61K 33/08
(Continued)

OTHER PUBLICATIONS

Culver Academy. Class of 1952 Newsletter. Obtained from https://alumni.culver.org/document.doc?id=517&chid=63 on May 17, 2017. Originally published on Oct. 10, 2013. 20 printed pages. (Year: 2013).*

(Continued)

*Primary Examiner* — Isaac Shomer
(74) *Attorney, Agent, or Firm* — Culhane Meadows PLLC; Robert C. Klinger

(57) ABSTRACT

A composition including a plant medium and a poly-oxygenated metal hydroxide that comprises a clathrate containing oxygen gas molecules. The poly-oxygenated metal hydroxide may comprise of a poly-oxygenated aluminum hydroxide. The composition may include one or more nutrients. The composition may be in a solid form, a fluid form, or a combination thereof. The poly-oxygenated aluminum hydroxide is soluble in a fluid. In one embodiment, the poly-oxygenated metal hydroxide composition may have particles having a diameter of 212 μm or less, and which may be homogeneous.

19 Claims, 13 Drawing Sheets

Related U.S. Application Data which is a continuation-in-part of application No. 15/648,312, filed on Jul. 12, 2017, now Pat. No. 9,950,006, which is a continuation-in-part of application No. 15/493,688, filed on Apr. 21, 2017, now Pat. No. 9,980,909, which is a continuation of application No. 15/188,586, filed on Jun. 21, 2016, now abandoned.

(60) Provisional application No. 62/315,524, filed on Mar. 30, 2016, provisional application No. 62/433,008, filed on Dec. 12, 2016.

(51) Int. Cl.
*A61K 9/00* (2006.01)
*C01F 7/02* (2006.01)
*A61K 9/16* (2006.01)
*B82Y 5/00* (2011.01)
*A61K 9/51* (2006.01)

(52) U.S. Cl.
CPC ........ *A61K 9/1682* (2013.01); *A61K 47/6949* (2017.08); *B82Y 5/00* (2013.01); *C01F 7/02* (2013.01); *C01F 7/023* (2013.01); *A61K 9/5115* (2013.01); *C01P 2004/61* (2013.01); *C01P 2004/62* (2013.01); *Y10S 977/773* (2013.01)

(56) References Cited

U.S. PATENT DOCUMENTS

| | | | |
|---|---|---|---|
| 9,950,006 B2* | 4/2018 | Woodmansee, Jr. | A61K 9/0026 |
| 10,137,146 B2* | 11/2018 | Woodmansee, Jr. | B82Y 5/00 |
| 10,137,147 B2* | 11/2018 | Bruce | A61K 33/08 |
| 10,137,148 B2* | 11/2018 | Bruce | A61K 33/08 |
| 2002/0132021 A1* | 9/2002 | Raskin | A01H 3/00 424/773 |

OTHER PUBLICATIONS

P Yang. "Investigating the Efficacy of a Novel Therapeutic to Mitigate Traumatic Brain Injury: Contributions of Environmental Exposures to Overall Healing." Masters Thesis, Baylor University, Aug. 2015. pp. i-vii and 1-80 (87 total sheets). (Year: 2015).*

J Gueldner, F Zhang, B Zechmann, ED Bruce. "Evaluating a novel oxygenating therapeutic for its potential use in the advancement of wound healing." Toxicology in Vitro, vol. 43, 2017, pp. 62-68. (Year: 2017).*

* cited by examiner

Figure 5. Scanning Electron micrograph of Ox66™ particle following nano-engineering. Magnification = 8000x Figure 6. Scanning Electron micrograph of Ox66™ following nano-engineering. Magnification = 10,000x Figure 7. Scanning Electron micrograph of Ox66™ following nano-engineering. Magnification = 10,000x

Particle Size: 26-45 μm

| | C | O | Al | Cl | (By % weight) |
|---|---|---|---|---|---|
| Spot 1 | 0.00 | 0.00 | 0.00 | 0.00 | |
| Spot 2 | 56.80 | 35.02 | 8.18 | 0.00 | |
| Spot 3 | 0.00 | 0.00 | 38.40 | 0.00 | **F |
| Spot 4 | 63.12 | 30.14 | 6.74 | 0.00 | |
| Spot 5 | 0.00 | 33.91 | 6.93 | 0.00 | |

Particle Size: 46-106 μm

| | C | O | Al | Cl | (By % weight) |
|---|---|---|---|---|---|
| Spot 1 | 0.00 | 54.49 | 39.35 | 0.00 | **F |
| Spot 2 | 1.90 | 55.46 | 37.55 | 0.00 | **F |
| Spot 3 | 1.34 | 60.58 | 36.74 | 0.00 | **F |
| Spot 4 | 0.00 | 57.12 | 42.88 | 0.00 | |

Particle Size: 107-212 μm

| | C | O | Al | Cl | (By % weight) |
|---|---|---|---|---|---|
| Spot 1 | 0.00 | 58.22 | 34.64 | 0.00 | *F |
| Spot 2 | 0.00 | 56.08 | 36.26 | 0.00 | *F |
| Spot 3 | 0.00 | 62.85 | 37.15 | 0.00 | *F |

Particle Size: 300-425 μm

| | C | O | Al | Cl | (By % weight) |
|---|---|---|---|---|---|
| Spot 1 | 0.00 | 41.72 | 41.75 | 16.53 | |
| Spot 2 | 0.00 | 53.53 | 31.01 | 15.46 | |
| Spot 3 | 0.00 | 57.41 | 25.74 | 16.85 | |
| Spot 4 | 0.00 | 54.62 | 29.29 | 16.10 | *F |

Particle Size: 426-500 μm

| | C | O | Al | Cl | (By % weight) |
|---|---|---|---|---|---|
| Spot 1 | 82.05 | 17.95 | 0.00 | 0.00 | |
| Spot 2 | 0.00 | 59.26 | 26.07 | 14.67 | |
| Spot 3 | 0.00 | 49.57 | 18.42 | 32.00 | |
| Spot 4 | 0.00 | 29.16 | 25.31 | 45.52 | *F |

FIGURE 8

| Identity | Aluminum hydroxide | Aluminum oxide | Aluminum hydroxide oxide | Ox66™ |
|---|---|---|---|---|
| Other name | "Hydrated alumina" | "Alumina" | "Aluminium oxyhydroxide" or "Boehmite" | "Poly-oxygenated aluminum hydroxide" |
| Chemical formula | Al(OH)$_3$ | Al$_2$O$_3$ | AlO(OH); AlHO$_2$ | Al$_{12}$H$_{12}$O$_{36}$; Al(OH)$_3$•6O$_2$ (reduced) |
| Molecular weight | 78.00 g/mol | 101.96 g/mol | 59.99 g/mol | 942.09 g/mol (110.00 g/mol reduced) |
| CAS Number | 21645-51-2 | 1344-28-1 | 24623-77-6 | None |
| Free (available) oxygen gas | None | None | None | 6 |
| Appearance | White amorphous powder | White solid | White crystal | Light blue powder |
| Density | 2.42 g/cm$^3$ | 4.1 g/cm3 | 3.01 g/cm$^3$ | 3.5 g/cm3 |
| Solubility in water | 0.0001 g in 100 mL | Insoluble in water | Insoluble in water | 1 g/100 mL (20 °C) |

FIGURE 10

PLANT MEDIUM INCLUDING AN OXYGEN-ENABLED COMPOSITION

TECHNICAL FIELD

The disclosure relates generally to a plant medium, such as soil, a liquid, or material including a poly-oxygenated metal hydroxide composition providing free oxygen for sustaining the life and growth of the plant.

BACKGROUND

Oxygen is one of the fundamental building blocks of life. Oxygen sustains life, but it also has therapeutic (i.e. healing) powers when delivered topically to tissue, orally for digestion, anally, vaginally, aerosolized for inhalation, injected to intramuscular tissue, intravenously to the blood circulatory system, and other delivery methods. Conventional oxygen therapies are commonly comprised of a gaseous delivery of oxygen (i.e. $O_2$) in chambers, such as hyperbaric oxygen therapy (HBOT). However, the concentration of oxygen delivered by gas is rather small, and the chambers are both expensive and not widely available.

A poly-oxygenated metal hydroxide manufactured and marketed by Hemotek, LLC of Plano, Tex. as Ox66™, the Assignee of this application, is a clathrate containing oxygen gas molecules that has been proven to have numerous therapeutic benefits. The Ox66™ composition is provided in powder form and is described as a non-homogenous size particle population, typically ranging from about 50 to 800 micrometers (μm).

Ox66™ exists under STP (standard temperature and pressure) as a poly-oxygenated aluminum hydroxide comprising a clathrate, and chlorine. A clathrate is a chemical substance consisting of a lattice that traps or contains molecules. The molecules trapped or contained within the clathrate are oxygen gas ($O_{2(g)}$). The chemical formula of the clathrate is $Al_{12}H_{42}O_{36}$, which mathematically is reduced to the molecular formula $Al(OH)_3.6O_2$. The 6 free oxygen gas molecules ($O_{2(g)}$) are separate from the oxygen molecules covalently bound in the hydroxide complex. The hydrogen is effervescent. The poly-oxygenated aluminum hydroxide is soluble in a fluid.

Plants, including trees, bushes, flowers, vegetable plants and fruit trees, and so forth all derive water, nutrients and oxygen through their roots from soil or a substance proximate their roots to sustain life and growth. The soil or substance is referred to as a plant medium throughout this application. Plants can grow in soil of the earth, and are also grown in controlled environments including greenhouses and vertical farming environments. Technology has enabled a massive variety of food, at a significantly reduced cost, and with fewer resources used for production.

There is an increasing need to optimize and fortify plants, such as the food supply chain to achieve more reliable, predictable, and nutritious ways to obtain basic sustenance. There is also a need to sustain the life of plants during transfer, such as during transplantation of plants, and also cut/grafted portions of the plants, such as moving produce to market and cut flowers from around the world.

SUMMARY

A composition including a plant medium and a poly-oxygenated metal hydroxide that comprises a clathrate containing oxygen gas molecules. The poly-oxygenated metal hydroxide may comprise of a poly-oxygenated aluminum hydroxide. The composition may include one or more nutrients. The composition may be in a solid form, a fluid form, or a combination thereof. The poly-oxygenated aluminum hydroxide is soluble in a fluid. In one embodiment, the poly-oxygenated metal hydroxide composition may have particles having a diameter of 212 μm or less, and which may be homogeneous.

BRIEF DESCRIPTION OF THE FIGURES

FIG. 8 is a chart illustrating the filtered Ox66™ composition at different particle sizes, obtained using a Scanning Electron Microscope (SEM) with Energy dispersive X-ray spectroscopy (EDS) analyzing various spots of the filtered Ox66™ composition;

FIG. 10 illustrates the solubility of the poly-oxygenated aluminum hydroxide in a fluid;

DETAILED DESCRIPTION

Figure 1:
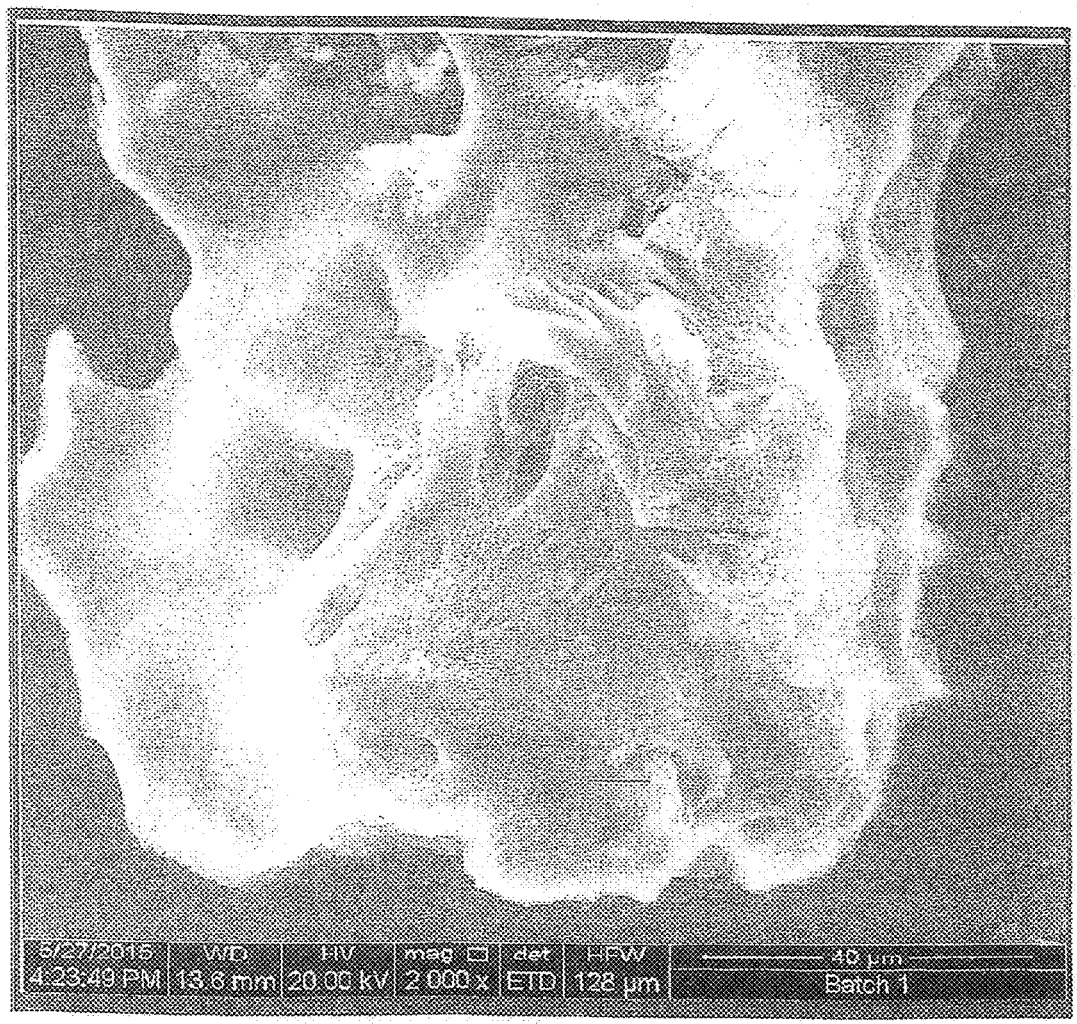
FIG. 1 is a scanning electron microscopy (SEM) image of a single 50 micrometer (μm) Ox66™ particle.

The following description of example embodiments provides information that enables a person skilled in the art to make and use the subject matter set forth in the appended claims, but may omit certain details already well-known in the art. The following detailed description is, therefore, to be taken as illustrative and not limiting. Objectives, advantages, and a preferred mode of making and using the claimed subject matter may be understood best by reference to the accompanying drawings in conjunction with the following detailed description of illustrative embodiments.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment.

However, as should be recognized by those skilled in the art, this frame of reference is merely a descriptive expedient rather than a strict prescription.

Nanoparticles are routinely defined as particles with sizes between about 1 and 1000 nm that show physical or chemical properties that are not found in bulk samples of the same material.

Dissolved oxygen refers to micrometer or nanometer sized bubbles of gaseous oxygen (mixed in water or other aqueous solution) made bioavailable to organisms, animals, or humans for respiration.

Aqueous medium means pertaining to, related to, and similar to water (the most common solvent on Earth).

Particles having a diameter of less than or equal to 70 nm do not create an immune response of the mammal.

Ox66™ particles are non-toxic poly-oxygenated aluminum hydroxide complexes comprising a clathrate containing oxygen gas molecules, stored and solubilized in either a 1-99% by weight aqueous solution, or as a dried powder, and are available from Hemotek LLC of Plano, Tex. The material is non-flammable, water-soluble, and slightly basic. Particle diameter sizes typically vary between 50 and 800 μm. These particles can also be described as a non-corrosive and non-vapor producing powder. Its appearance is white to slightly blue as a powder with mass but very little weight (i.e. one gallon weighs less than 4.3 ounces), or a clear slightly viscous liquid when solubilized in an aqueous solution.

The inventive concepts disclosed and claimed in this application relate generally to a chlorine-free poly-oxygenated aluminum hydroxide composition comprising a clathrate containing oxygen gas molecules that is soluble. These chlorine-free particles have a diameter of less than or equal to 212 μm, and enable numerous revolutionary applications and treatments that provide significant achievements in bioscience. Through research and clinical studies, these particles have been proven to treat body conditions of mammals, including humans and animals, with astounding success and efficiency. This will be described in more detail with respect to FIG. 8 shortly.

According to exemplary embodiments of this disclosure, through research, studies and clinical studies, it has been discovered that engineering the Ox66™ particles to have diameter sizes at or below 3 μm opens up significant and revolutionary new opportunities for oxygen therapy. Providing particles having diameters of 3 μm is critical to achieve numerous new applications, such as by oral, nasal, intravenous and topical delivery, to treat conditions and diseases in revolutionary ways. Several of the new applications and treatments are disclosed herein.

One exemplary embodiment is delivering poly-oxygenated aluminum hydroxide particles intravenously as a resuscitative fluid, and to treat diseases of organs when the diameter of the particles is in the range of 250 nm to 1000 nm. Particles having diameters between 250 to 1000 nm will stay in the capillary, vein, or artery linings of the circulatory system and not passively diffuse past the lining into surrounding tissue.

Another exemplary embodiment is delivery, by aerosol when inhaled, for absorption of the poly-oxygenated aluminum hydroxide particles through the lung tissue when the particles are reduced to 250 nm and less. Such an application effectively treats internal burns. Particles having a diameter size from 1 to 3000 nm deposit into the deep airway ducts and diffuse evenly within the alveolar or gas exchange regions of the lung.

A remarkable example is delivering the poly-oxygenated aluminum hydroxide particles intravenously to treat traumatic brain injury (TBI) when the diameter of the particles is reduced to about 300 nm and less so that the particles can traverse the brood brain barrier (BBB). This application can also be used to treat strokes, chronic traumatic enchepelopathy (CTE), and perhaps even cancer.

There is a significant biophysical difference between a 50 μm particle and a 3 μm particle. After intravenous administration, 50 μm particles are larger and have more mass than 3 μm particles, therefore they tend to absorb onto the linings of the veins. Three (3) μm particles stay in circulation much longer, have much less mass, and have higher surface area. After inhalation administration, 50 μm diameter particles deposit in the oral or nasal cavity and do not reach even the upper airways of the lung. Three (3) μm diameter particles are small enough to deposit in the very deep lung and perfuse out to the lung lining. After topical administration, 50 μm diameter particles tend to stay on the surface of the epidermis and eventually wash off the skin completely. Three (3) μm diameter particles penetrate through the epidermis and dermis layers of the skin and reside in the subcutaneous layer of the skin. After oral administration, 3 μm diameter particles absorb through the lining of the esophagus and stomach. Fifty (50) μm diameter particles reside in the stomach for up to 4 hours, dissolve (or break-down) and lose their oxygen carrying capability.

Another exemplary embodiment includes increasing the oxygen content of fluids with nanometer-sized Ox66™ particles, such as water, sports drinks, and nutritional drinks, which provides many benefits and applications. The nanometer-sized Ox66™ particles have been clinically shown to pass through the stomach, duodenum, and intestinal walls into the bloodstream of the body, and are not simply absorbed by the stomach lining. One method for increasing the dissolved oxygen content in an aqueous medium includes sparging the aqueous medium with air, oxygen or oxygen-enriched air.

In another exemplary embodiment, the nanometer-sized Ox66™ particles, either as a powder or in a carrier such as a gel or lotion, have also been clinically proven to increase the level of localized oxygen in injured tissues to accelerate the healing process.

Figure 2:
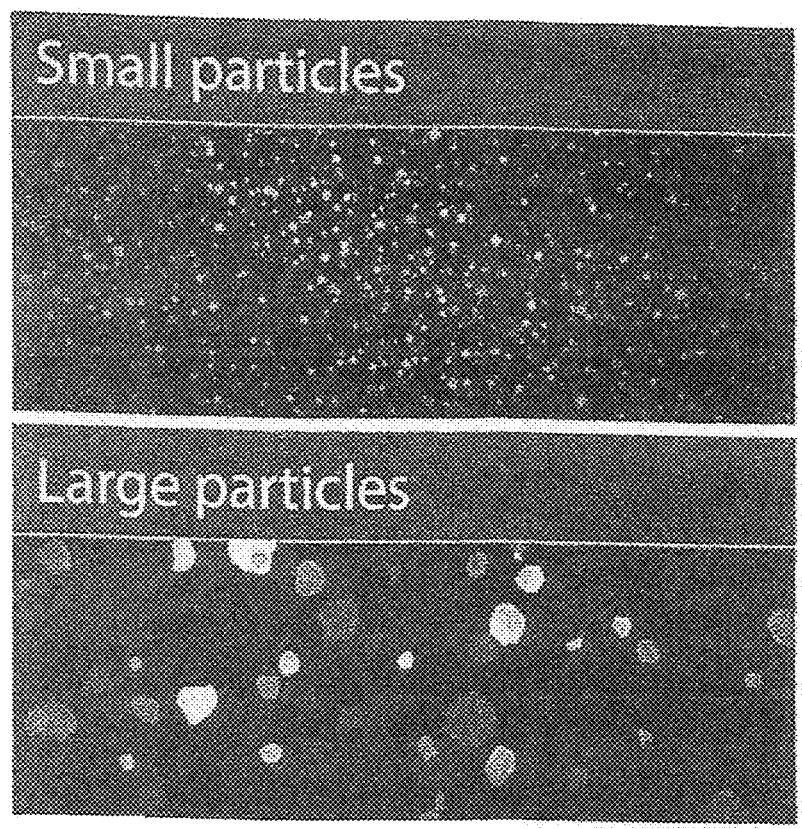
FIG. 2 is a graphic art image of the jagged shaped Ox66™ particle population.

FIG. 1 is a scanning electron microscopy (SEM) image of a single 50 micrometer (μm) Ox66™ particle. A 50 μm particle is easily aerosolized, but it is well outside the respirable range of 1-3 μm. A 50 μm particle has little density due to its chemical composition and its porosity. FIG. 2 is a graphic art image of the jagged shaped Ox66™ particle population.

Controlled milling is defined as a machining procedure using vessels accelerating in a rotary or planetary motion to decrease the size of the primary particles from micrometer sized to nanometer sized materials. Milling covers a wide array of procedures, operations, tools, and machines. The resultant nanometer sized particle can be accomplished using small instruments or large milling machines. Example milling instruments include: "milling machine", "machining centers", or "multitasking machines".

Figure 3:
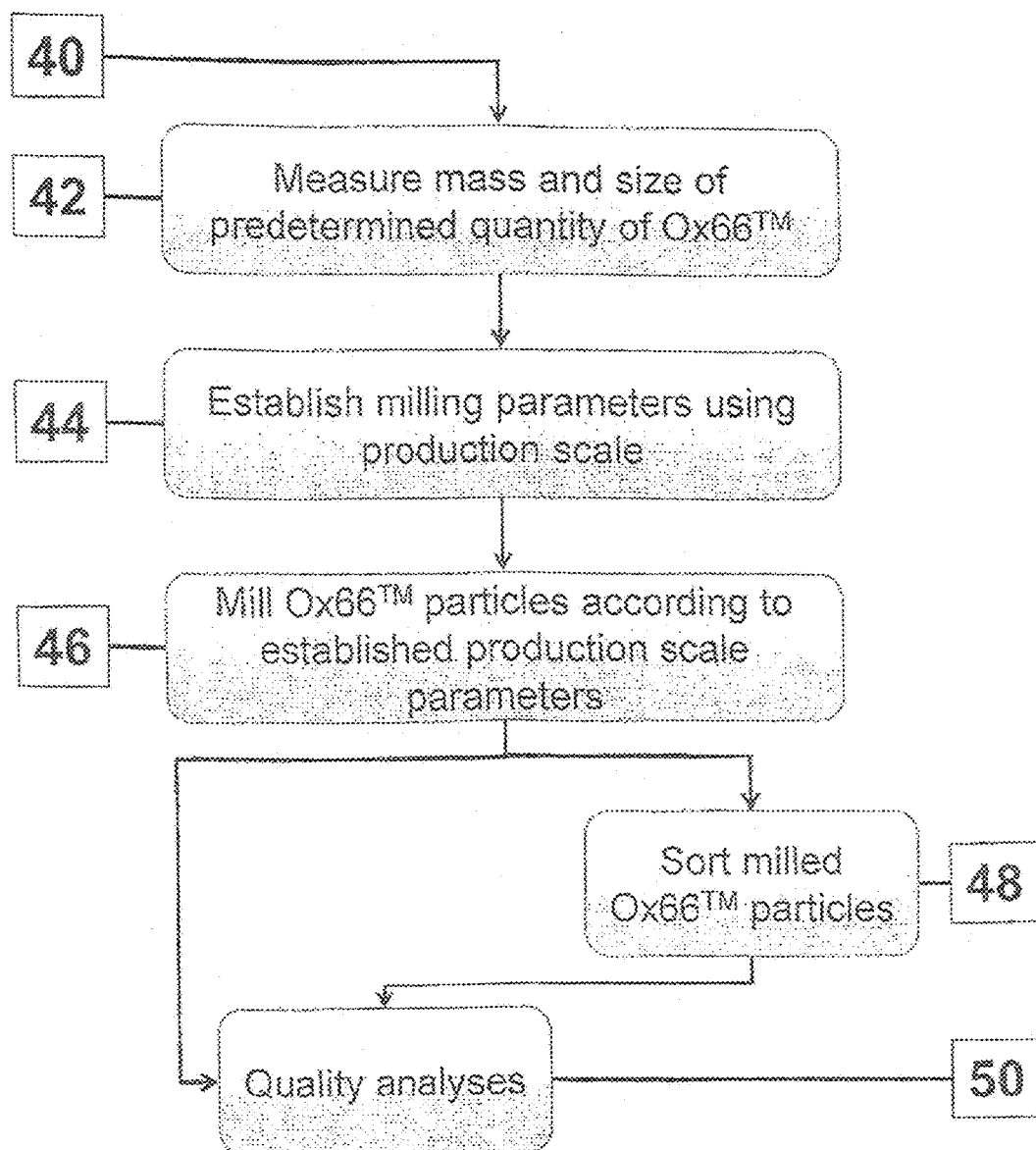
FIG. 3 depicts one exemplary process used to create nano-engineered Ox66™ nanoparticles to exploit the physical and chemical properties of each particle-type.

Referring to FIG. 3, there is shown an exemplary process shown at 40 for forming nanosized Ox66™ particles having diameter sizes of 3 μm or less using a planetary motion milling machine.

At step 42, a predetermined quantity of the quality assured Ox66™ powdered material is measured, and placed in a container.

Figure 5:
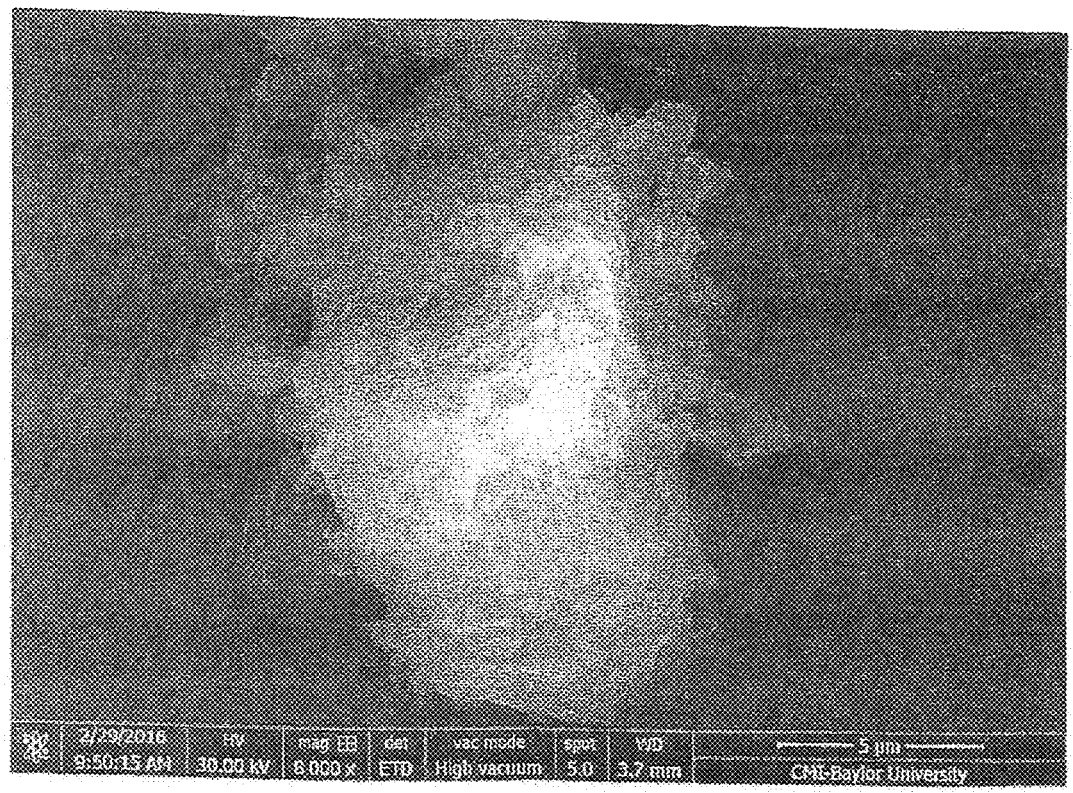
FIGS. 5-7 are scanning electron microscopy (SEM) images showing the nano engineered Ox66™ particles at different image magnifications having particle diameters at 3 μm and below.

At step 44, a milling scale is used to establish parameters of the generating particles having a diameter of 3 μm or less, such as shown in FIG. 5, both for small-scale production as well as mass production. The milling procedure is dependent upon the features of the ball mill, which may be a planetary motion device, such as Retsch Planetary Ball Mill PM 100, 200, or 400 or United Nuclear Scientific Equipment 'Hobby" Ball Mill. The milling procedure identifies several variables, including a quantity of Ox66™ material, the rotation rate, the size of the milling beads, the type of milling beads, and the time of milling to achieve desired size of the Ox66™ particles. For example, the rotation rate may be for at least 1 minute up to 1,440 minutes at a rotation rate of at least 100 up to 10,000 rotations per minute.

Figure 4:
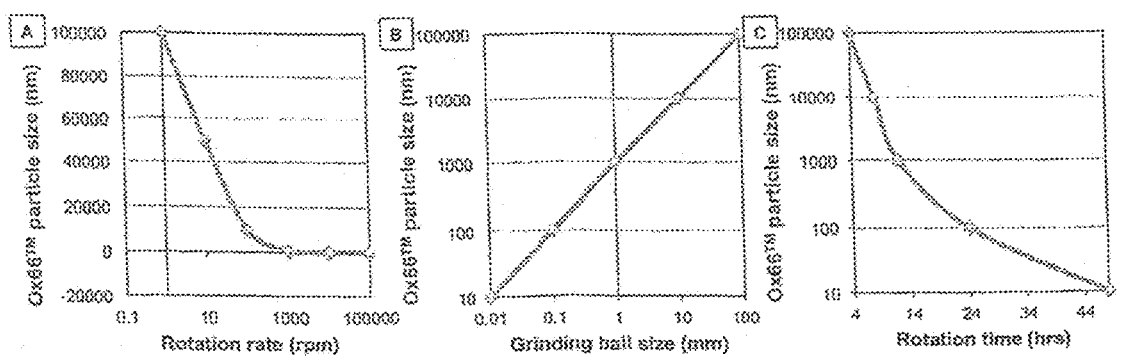
FIG. 4 illustrates three different graphs modeling the effect of Ox66™ particle size when varying (A) rotation rate, (B) grinding ball size, and (C) rotation time.

FIG. 4 includes three different graphs modeling the effect of Ox66™ particle size when varying (A) rotation rate, (B) grinding ball size, and (C) rotation time. As rotation rate, measured in rotations per minute (rpm) increases, particle size decreases. As grinding ball size, measured in millimeters (mm) decreases, particle size decreases. As rotation time, measured in hours (hrs) increases, particle size decreases.

At step 46, the predetermined quantity of Ox66™ particles are then milled in a controlled manner in a planetary motion ball mill, according to the milling procedure to achieve a desired homogenous size of the Ox66™ particles. The Ox66™ particles are milled or ground down under high energy in the presence of a milling media, such as highly reticulated polystyrene or zirconium milling beads. The Ox66™ particles are recirculated, re-milling them until a consistent product is generated.

Optionally, at step 48, additional sorting may be performed.

At step 50, the homogeneous milled Ox66™ particles are subjected to quality analysis to confirm sizing and consistency. If the Ox66™ particles are not consistent, they may be further milled to achieve the desired sizing.

The milling media can also abrade under the conditions of milling, so care is taken such that significant contamination of the nanosuspension by the milling media does not occur. Nanosuspension is defined as a submicron colloidal dispersion of drug particles.

The resultant Ox66™ particles have a primary particle size of 3 μm or less. In one exemplary embodiment, the reduced size particles are then separated into homogeneous sizes in an effort to exploit the physical and chemical properties of each particle-type. Sieves can be used to sort out particles by sizes to create homogeneous sizes of particles, such as sieve shakers manufactured by Endecotts Ltd of London, UK. Different size sieve filters are used to obtain selected particle sizes.

One homogenous size of particles may be particularly beneficial for treating a particular body condition, such as 300 nm (or less) diameter particles to treat traumatic brain injury (TBI). Another homogenous size of particles may be beneficial for providing a resuscitative fluid (RF) to increase the tissue oxygenation ($PO_2$), such as using 2 μm-4 μm diameter particles which do not trigger an immune response. Generating nanometer sized particles increases the in vivo (i.e. in a whole, alive organism) dissolution rate and fraction absorbed to increases oral bioavailability.

Figure 6:
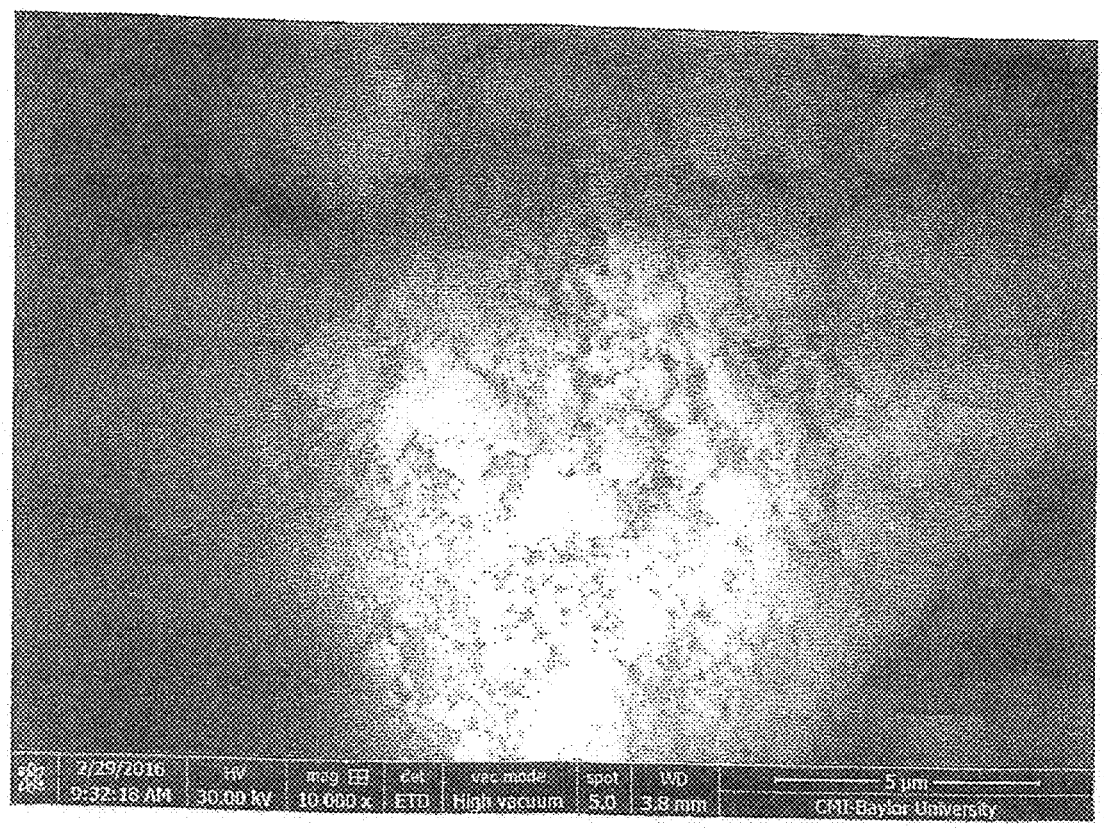
Figure 7:
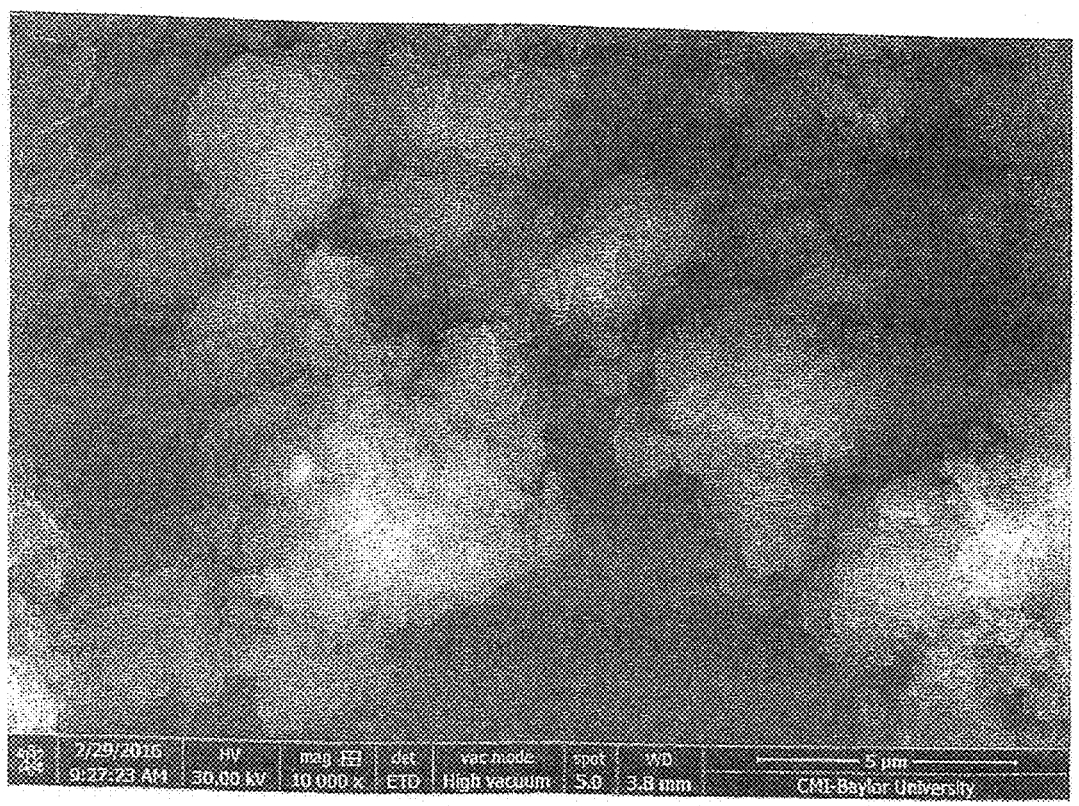

FIGS. 5-7 are scanning electron microscopy (SEM) images showing the nano-engineered Ox66™ particles at different image magnifications, showing the particle diameters at 3 μm and below.

The pharmaceutical preparation of nanomaterial-based dosage forms is encouraged by a number of pharmaceutical drivers; for compounds whose water solubility or dissolution rate limits their oral bioavailability, size reduction into the nanometer size domain can increase in viva dissolution rate and fraction absorbed.

The process to generate a homogeneous nanometer size particle population can also be of use in the design of parenteral dosage forms wherein poorly soluble drugs can be "milled" to a specified size and size range resulting in not only useful bioavailability but also sustained release features.

The development of drug particles within the nanometer size regime of 1 to 1000 nm involves a top-down approach in which the active ingredient is milled (or otherwise subjected to particle reduction strategies) in either an aqueous environment or in a dry formulation; top-down strategies are considered more controllable and more robust as a function of process and design space for this type of manipulation.

DESCRIPTION OF EXAMPLE EMBODIMENTS

Chlorine-Free Poly-Oxygenated Aluminum Hydroxide

Referring now to FIG. 8, according to another embodiment of this disclosure, a composition of chlorine-free poly-oxygenated metal hydroxide comprises a clathrate containing oxygen gas molecules. The composition is soluble.

The chlorine-free poly-oxygenated metal hydroxide composition is beneficial in a therapeutic quantity when delivered to a mammal, including, but not limited to, oral, topical, nasal, vaginal, anal, and intravenously administration. The composition is poly-oxygenated because it has oxygen gas ($O_{2(g)}$) that is free to move in the composition molecules, and which oxygen gas is bioavailable to oxygenate the mammal.

In one exemplary embodiment, the chlorine-free poly-oxygenated metal hydroxide is a composition of filtered poly-oxygenated aluminum hydroxide Ox66™ composition. The poly-oxygenated aluminum hydroxide composition is free of chlorine residuals and may be homogeneous. Homogeneous as used in this application means that the sizes of the particles fall in a tight range of sizes, such as between 107-212 um, 46-106 um, and 26-45 um. It has been discovered that Ox66™ particles having a diameter of less than or equal to about 212 um are free of chlorine residuals and particles. Applicant sorted the Ox66™ composition by size into batches, and discovered that filtered particles having a diameter less than about 212 um had a noticeably different texture and feel. Upon further investigating using a calibrated Scanning Electron Microscope (SEM) laboratory instrument to analyze various spots of the composition for different size ranges, it was discovered that such particles under 212 um were free of chlorine particles and residuals, as supported in the test results shown in FIG. 8.

FIG. 8 illustrates the composition of filtered Ox66™ at different particle sizes, where there is shown five tables, obtained using a Scanning Electron Microscope (SEM) with Energy-dispersive X-ray spectroscopy (EDS).

As shown in the bottom table in FIG. 8, the data obtained from analyzing four (4) spots of the Ox66™ composition in a batch of homogeneous Ox66™ particles each having a diameter between 426-500 um is shown. The first spot reflects analyzing the substrate having carbon. The data from analyzing the other 3 spots shows the percentage of chlorine varying between 14.67% and 45.52%, which is very significant. It is noted the detected carbon component in some samples is part of the substrate media that the composition is prepared upon during testing, and the carbon is not part of the composition itself.

As shown in the table second from the bottom of FIG. 8, the data obtained from analyzing four (4) spots of the Ox66™ composition in a batch of homogeneous Ox66™ particles having a diameter between 300-425 um is shown. The data from analyzing the 4 spots shows the percentage of chlorine varying between 15.46% and 16.85%. These are significant percentages of chlorine, and the chlorine is undesirable in many products, treatments and therapies as they can create adverse results and reactions.

As shown in the three upper tables in FIG. 8, the data obtained from analyzing spots of the Ox66™ composition in different batches of Ox66™ particles having a diameter of less than 212 um shows the composition is entirely free of chlorine in all spots. This is true for the batches of homogeneous Ox66™ particles having a diameter between 26-45 um, 46-106 um, and 107-212 um, as shown. This is significant and highly beneficial as previously described.

The composition comprising chlorine-free particles having diameters sized at or below 212 um have tremendous uses in products, treatments and therapies. For instance, the chlorine free composition is not a desiccant, which makes it ideal in some products, including cosmetics where maintaining moisture is preferred. A desiccant is a hygroscopic substance that induces or sustains a state of dryness (desiccation) in its vicinity. Commonly encountered pre-packaged desiccants are solids that absorb water. Chlorine is fairly reactive with water and oxygen and acts as a desiccant in particle systems. The Ox66™ composition is often, but not always, better suited when chlorine is absent in the formulation because of the desire to maximize the amount of oxygen in the product to improve efficacy. Cosmetic products including creams, moisturizers, serums, etc. tremendously benefit from the oxygen carrying properties of the Ox66™ composition, as well as the chlorine free composition of this disclosure.

It is noted that for larger particle suspensions in water, chlorine may be desired for stability, and for certain uses where chlorine is a benefit, such as when used as a desiccant.

A formulation without chlorine is a more simple and streamlined compound that saves time, money, and resources. A quantity of such chlorine-free particles has a softer feel and is less abrasive than the composition including chlorine, making the composition suitable for cosmetics that have demanding requirements from both manufacturers and customers.

Using the electron mapping analytical technique, it was determined that Ox66™ contains very few elements from the periodic table. These elements include aluminum (Al), hydrogen (H), and oxygen (O), and chlorine (Cl). On Earth, the most stable material that includes the first of these three elements is commonly referred to as "aluminum hydroxide". And the most stable aluminum hydroxide chemical formula is $Al(OH)_3$. The aluminum hydroxide is seen as a clathrate including free oxygen gas $O_2$, and the chlorine is a separate particle.

A chemical formula is an expression which states the number and type of atoms present in a molecule of a substance.

After further analytical analyses using energy dispersive X-ray spectroscopy on the aluminum hydroxide clathrate, it was subsequently deduced that the balanced mass ratio (at the elemental level) of the aluminum hydroxide portion of Ox66™ includes 12 aluminum (Al) atoms, 42 hydrogen (H) atoms, and 36 oxygen (O) atoms. Simply put, this chemical formula is represented as is $Al_{12}H_{42}O_{36}$.

The relationship between $Al(OH)_3$ and $Al_{12}H_{42}O_{36}$ is substantiated when additional analytical techniques confirm the presence or absence of other stable molecules associate with the Ox66™ material. These other molecules include $H_2$, $O_2$, and $H_2O$. There is strong evidence that supports that $O_2$ gas is present—and that the quantity of the molecules is approximately 6:1 in ratio of $O_2:Al(OH)_3$. There is no evidence to suggest that the Ox66™ material includes $H_2$ or $H_2O$ molecules in its system.

Hydrogen (H) atoms, when combined in their simplest configuration, forms hydrogen gas ($H_2$). These molecules are effervescent and have the potential to evacuate the aluminum hydroxide Ox66™ clathrate structure very easily since $H_2$ molecules are very small. In fact, the diameter of a hydrogen gas molecule is smaller than the estimated pore size of the aluminum hydroxide Ox66™ clathrate structure.

Since there is no evidence that water ($H_2O$) molecules are present in the Ox66™ material structure, and because there is no evidence that oxygen ($O_2$) gas is present, it is extrapolated that the Ox66™ chemical formula $Al_{12}H_{42}O_{36}$ re-arranged to a molecular formula $Al_{12}(OH)_{36}$ with ~6 oxygen gas molecules present and ~12 hydrogen gas molecules escaped.

Molecular formula is a formula giving the number of atoms of each of the elements present in one molecule of a specific compound.

The reduced molecular formula can be hypothesized and represented as $Al(OH)_3.6O_2$.

FIG. 10 illustrates the solubility of the Ox66™ poly-oxygenated aluminum hydroxide in a fluid. As shown, the Ox66™ composition is soluble in a fluid up to 1 gram of Ox66™ composition per 100 ml of a fluid such as water, (1 g/100 ml).

Nutraceuticals

Figure 9A:
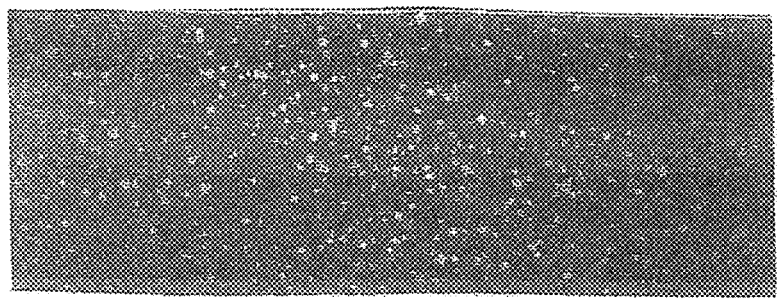
FIGS. 9A and 9B illustrate a composition including a poly-oxygenated aluminum hydroxide, and at least one nutrient, wherein the composition is in a fluid form or a powder form.
Figure 9B:
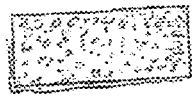

In one exemplary embodiment, the chlorine-free poly-oxygenated aluminum hydroxide composition is particularly well suited for use with or in nutraceuticals, including products configured to be orally ingested by a mammal. FIGS. 9A and 9B illustrate a composition including a poly-oxygenated aluminum hydroxide, such as the soluble poly-oxygenated aluminum hydroxide clathrate portion of the Ox66™ composition, and at least one nutrient, wherein the composition in a fluid form as shown in FIG. 9A, or in a powder form as shown in FIG. 9B.

A nutraceutical is defined as a pharmaceutical-grade and standardized nutrient. Such nutraceuticals include proteins, vitamins, fiber, and electrolytes that can be found in baby formula, health bars, and supplements, such as Similac®, PediaSure®, Pedialyte®, Glucerna®, and Ensure® products manufactured by Abbott Labs of Abbot Park, Ill., each of which is a U.S. Registered trademarks of Abbott Labs, Gerber® Good Start® products and Boost® products each manufactured by Nestle® of Switzerland. Other nutraceuticals can include, but are not limited to, performance enhancing products including Gatorade® branded products including fluids, powders, and bars.

One embodiment of an electrolyte nutraceutical configured to treat dehydration comprises a solution having a balance of sugar, electrolytes, and the Ox66™ composition providing oxygen gas contained in the clathrate. This nutraceutical is formulated with an optimal balance of sugar and electrolytes needed to help replenish vital fluids, minerals, and nutrients in the body, which, when lost, can lead to dehydration. The oxygen gas of the Ox66™ composition helps to oxygenate the human body which improves body function.

When the electrolyte nutraceutical is used as a treatment for hangovers, the oxygen gas helps speed up the breakdown of alcohol. Once absorbed by the bloodstream, the alcohol leaves the body in three ways: The kidney eliminates 5 percent of alcohol in the urine; the lungs exhale 5 percent of alcohol, which can be detected by breathalyzer devices; and the liver chemically breaks down the remaining alcohol into acetic acid.

The breakdown, or oxidation, of alcohol occurs in the liver, wherein an enzyme in the liver called alcohol dehydrogenase strips electrons from alcohol to form acetaldehyde. Another enzyme, called aldehyde dehydrogenase, converts the acetaldehyde, in the presence of oxygen, to acetic acid, the main component in vinegar. When the alcohol is oxidized to acetic acid, two protons and two electrons are also produced. The acetic acid can be further broken down into carbon dioxide and water.

As a rule of thumb, an average person can normally eliminate 0.5 oz (15 ml) of alcohol per hour. So typically, it would take approximately one hour to eliminate the alcohol from a 12 oz (355 ml) can of beer.

Advantageously, by consuming the electrolyte nutraceutical including the Ox66™ composition, the oxidizing and breakdown of the alcohol is accelerated in the human body due to the oxygen gas released by the clathrate into the bloodstream, thus reducing the time for the body to breakdown alcohol, and thus reducing the experienced effects of alcohol including intoxication, and the unwanted effects of hangovers.

In one exemplary embodiment, 1 mg of the Ox66™ composition is mixed with about 12 oz (355 ml) of a balanced sugar and electrolyte solution such as shown in FIG. 9A, although different ratios of this mix are acceptable. It is preferable to use the Ox66™ composition having particles each with a diameter of under 212 um as this embodiment does not include chlorine as previously described. An example is adding 4 mg of the Ox66™ composition with particles each having a diameter under 212 um to 33.8 oz (1 liter) of Pedialyte® Oral Electrolyte. Other embodiments include adding the Ox66™ composition with particles each having a diameter under 212 um to Pedialyte® kids and adult powder, and Pedialyte® freezer pops.

Another illustrative embodiment of a nutritional configured to ensure a healthy digestive system comprises one or more of a protein, vitamins, minerals, fiber, in addition to the Ox66™ composition. In one illustrative embodiment, 1 mg of the Ox66™ composition with particles each having a diameter under 212 um is added to 7 g protein and 25 vitamins and minerals, as well as 3 g fiber. One illustrative embodiment comprises adding 1 mg of the Ox66™ composition with particles each having a diameter under 212 um to an 8 fluid ounce (236 ml) of PediaSure® Grow and Gain with Fiber. The addition of the Ox66™ composition provides the additional benefit of free oxygen gas molecules that are beneficial to the digestive system of a mammal. It has been clinically proven at Baylor University in Waco, Tex. that the Ox66™ composition is absorbed into the body bloodstream through the stomach lining, and in addition, is passed into the upper intestine of the digestive system. The free oxygen gas molecules of the Ox66™ composition are advantageous to increase oxygen throughout the body.

In another embodiment, the Ox66™ composition with particles each having a diameter under 212 um is added to Ensure® branded adult products. Examples include Ensure® Original, Ensure® Plus, Ensure® Enlive, Ensure® High Protein, Ensure® Clear, and Ensure® Light. The Ox66™ composition is absorbed into the body bloodstream through the esophagus and stomach lining, and in addition, is passed into the upper intestine of the digestive system. The free oxygen gas molecules of the Ox66™ composition are advantageous to increase oxygen throughout the body. One illustrative embodiment comprises adding 1 mg of the Ox66™ composition with particles each having a diameter under 212 um to an 8 fluid ounce (236 ml) of Ensure® Enlive.

In another embodiment, the Ox66™ composition with particles each having a diameter under 212 um is added to Similac® branded or Gerber® Good Start® branded products for babies, toddlers, and nursing mothers. Illustrative examples include Similac® Pro-Advance, Similac® Advance Non-GMO, Similac® Advance, Similac® for Supplementation NON-GMO, Similac® Organic, and Similac® Pure Bliss infant formula. One illustrative embodiment comprises adding 1 mg of the Ox66™ composition with particles each having a diameter under 212 um to an 8 fluid ounce (236 ml) of a Similac® branded product. The Ox66™ composition with particles each having a diameter under 212 um can also be mixed with the commercial powered versions of the products such as Similac® Pro-Advance, as shown in FIG. 9B.

In another embodiment, the Ox66™ composition with particles each having a diameter under 212 um is added to Glucerna® branded products suitable for individuals with diabetes. One illustrative embodiment comprises adding 500 mg/ml of the Ox66™ composition with particles each having a diameter under 212 um to an 8 fluid ounce (236 ml) of a Glucerna® branded product, such as Glucerna® Snack Shakes, Glucerna® Hunger Smart Nutrition Shakes, and Glucerna® Therapeutic Oral Supplement. The Ox66™ composition with particles each having a diameter under 212 um can also be added to solid foods, such as Glucerna® Nutrition bars.

In another embodiment, products manufactured by Nestle® of Switzerland including the Boost® branded nutritional products are supplemented with the Ox66™ composition with particles each having a diameter under 212 um. As with the Abbot Labs® suite of products, one illustrative embodiment comprises adding 500 mg/ml of the Ox66™ composition with particles each having a diameter under 212 um to an 8 fluid ounce (236 ml) of a Boost® branded product, such as Boost® Original, Boost® High Protein, Boost® Glucose Control, Boost® Plus, and Boost® Calorie Smart. Some of these Boost® nutritional products are available in powders. The Ox66™ composition is mixed with the powder in proportion such that 500 mg/ml of the Ox66™ composition with particles each having a diameter under 212 um is provided in an 8 fluid ounce (236 ml) portion.

In another embodiment, nutritional products manufactured by Gatorade® of Chicago Ill., including Gatorade Recover® products including protein shakes, are supplemented with the Ox66™ composition with particles each having a diameter under 212 um. One illustrative embodiment comprises adding up to 500 mg/ml of the Ox66™ composition with particles each having a diameter under 212 um to an 8 fluid ounce (236 ml) of a Gatorade Recover® branded product.

In each of the embodiments of a composition described above comprising a nutraceutical and the Ox66™ composition with particles each having a diameter under 212 um, a preferred concentration is at least 1 milligram of the Ox66™ composition for every 8 fluid ounces of fluid, and up to 500 mg/ml.

IV Delivery

In one exemplary embodiment, the chlorine-free composition is also particularly well suited as a poly-oxygenated metal hydroxide that is intravenously (IV) deliverable to a mammal. Such IV deliverable products can include 75-90% colloid or crystalline solution with 10-25% addition of poly-oxygenated metal hydroxide particles. The poly-oxygenated metal hydroxide may have a concentration range of 0.1 mg/l to 1000 mg/l. The poly-oxygenated metal hydroxide may have particles that are surface modified.

In one example method of use, the chlorine-free composition is therapeutically beneficial to treat a depletion of hemoglobin in the mammal, wherein the poly-oxygenated metal hydroxide acts as an oxygen resuscitative fluid to treat hypoxia, increasing the interstitial tissue oxygenation $P_{ISF}$ $O_2$.

In other exemplary embodiments, products may include the chlorine-free composition in wound care, hair care, and skin care products. Such wound care products are configured to promote and accelerate the healing of skin wounds and lesions. Hair care products include products configured to reduce baldness and re-grow hair, as the bioavailable oxygen gas is beneficial to stimulate growth of hair follicles which may be oxygen deprived, and hair dyes. Skin care products can include lotions, gels and soaps, for example, that treat skin conditions, such as psoriasis and eczema.

The Ox66™ composition is:
configured to be therapeutically effective in treating a condition of a mammal; configured to be intravenously delivered to a mammal, such as to oxygenate the mammal; configured to not create an immune response of the mammal;
configured to penetrate through epidermis and dermis layers of skin and reside in a subcutaneous layer of the skin;
configured to absorb through lining of an esophagus, a stomach and a small intestine;
configured to traverse a brood brain barrier (BBB) of a mammal; and
configured to stay in a capillary, vein, or artery linings of a mammal circulatory system and not passively diffuse past a lining into surrounding tissue.

Plant Medium

Figure 11:
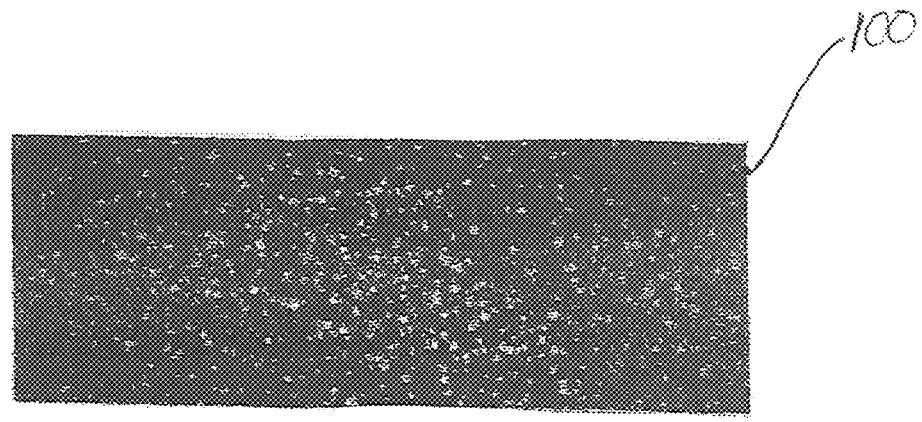
FIG. 11 illustrates a plant medium including a poly-oxygenated metal hydroxide that sustains the life and supports growth of a plant.

An illustrative embodiment of a plant medium 100 including a poly-oxygenated metal hydroxide is shown in FIG. 11, such as comprising Ox66™. The plant medium may be in a solid form, a fluid form, or a composition thereof, such as a gel or paste. Examples of a solid form include soil, dirt, sand, compost, a synthetic substance, a filler, just to name a few. Examples of a fluid form include a liquid, gas, gel, and solution comprised of two or more substances.

Figure 12:
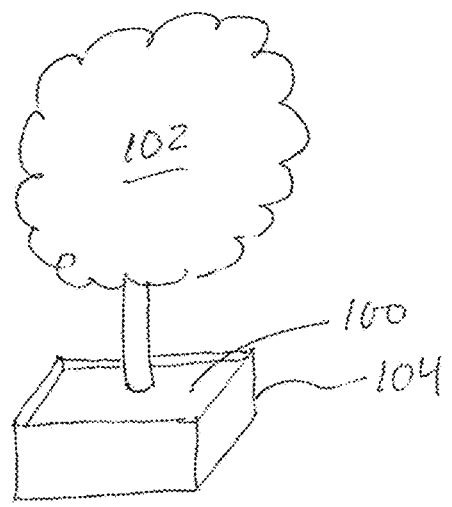
FIG. 12 illustrates a bush planted in a plant medium including a poly-oxygenated metal hydroxide.

In one embodiment, a plant 102 is planted in the plant medium 100 including a poly-oxygenated metal hydroxide, such as Ox66™, as shown in FIG. 12. A plant is defined in this application as a living organism of the kind exemplified by trees, shrubs, herbs, grasses, ferns, and mosses, typically growing in a permanent site, absorbing water and inorganic substances through its roots, and synthesizing nutrients in its leaves by photosynthesis using the green pigment chlorophyll. FIG. 12 illustrates a bush planted in a receptacle 104 containing a quantity of the plant medium 100 mixed with a quantity of the poly-oxygenated metal hydroxide, having the freely available $O_2$. This freely available $O_2$ helps the plant grow faster and healthier, and may help resist disease. For instance, 1 cubic ft. of the plant medium comprising soil is mixed with 2 ounces of the poly-oxygenated metal hydroxide, although other concentrations are within the scope of this disclosure. All the plant medium in the receptacle can be thoroughly mixed with the poly-oxygenated metal hydroxide, or just a subpart thereof. For instance, only the plant medium proximate and about the roots of the plant can be mixed with poly-oxygenated metal hydroxide, and/or the surface of the plant medium. The plant medium can include at least one nutrient, such as a fertilizer comprises of nitrogen and phosphorus, in a liquid or solid form, such as granules.

The plant medium can also include a fluid comprising a solution including a liquid and the poly-oxygenated metal hydroxide, and at least one nutrient. For instance, a solution having a concentration of at least 1 milligram of the poly-oxygenated metal hydroxide to 8 fluid ounces of a fluid, such as water, and a nutrient. In one embodiment, the poly-oxygenated metal hydroxide can be completely solubilized in the fluid, and in another embodiment only a portion of the poly-oxygenated metal hydroxide is solubilized in the fluid. As shown in FIG. 10 and previously discussed, the poly-oxygenated metal hydroxide is soluble up to 1 gram per 100 mL of fluid.

The particle sizes of the poly-oxygenated metal hydroxide used in the plant medium can be of any size in one embodiment. In another embodiment, the poly-oxygenated metal hydroxide can be comprised of particles having a size at or below 212 um so that there is no chlorine in the poly-oxygenated metal hydroxide. The poly-oxygenated metal hydroxide may be homogenous in an embodiment.

Figure 13:
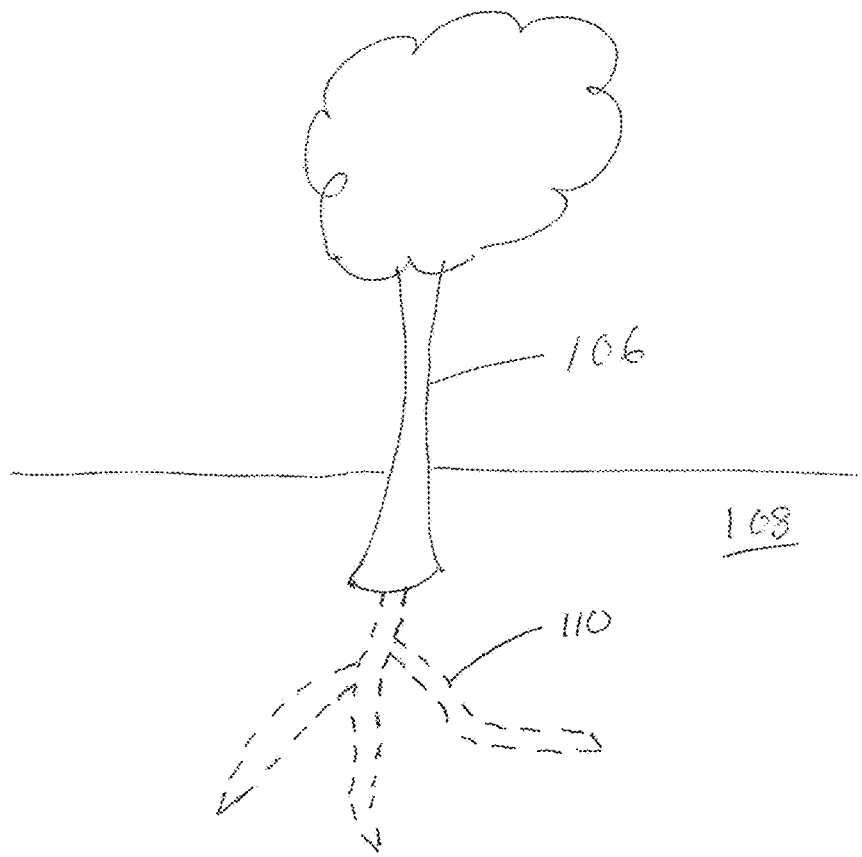
FIG. 13 illustrates a tree planted in the earth including a poly-oxygenated metal hydroxide.

As shown in FIG. 13, a plant planted in the earth has the poly-oxygenated metal hydroxide distributed on top of the soil about the plant, or within an upper portion of the soil about the plant. FIG. 13 illustrates a tree 106 planted in the earth 108, where the plant medium disposed about the roots 110 of the plant is mixed with the poly-oxygenated metal hydroxide. The plant can also be watered with the fluid comprising the poly-oxygenated metal hydroxide. The roots can absorb the oxygen gas $O_2$ in the poly-oxygenated metal hydroxide and thus the plant grows vigorously and better sustains life. Fruit and flowers on the tree grow better in terms of quality, and quantity due to the readily available oxygen gas absorbed the tree roots. Watering of the tree can help improve the intake of the oxygen gas freely available $O_2$ in the plant roots, in part because the poly-oxygenated metal hydroxide is soluble in the water and better distributes about the root system.

Figure 14:
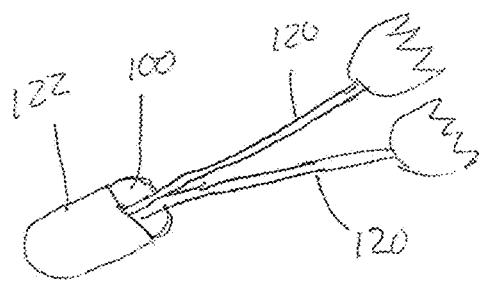
FIG. 14 illustrates cut flowers having flower stems disposed in a plant medium including a poly-oxygenated metal hydroxide.

FIG. 14 shows an embodiment illustrating multiple flowers 120 cut from a bush or tree, with the cut ends of the flower stems enveloped with the plant medium 100 including the poly-oxygenated metal hydroxide within a vessel 122. For instance, a liquid such as water includes the solubilized poly-oxygenated metal hydroxide such that the flower stems absorb the freely available oxygen gas and the flowers remain healthy and fresh a longer period of time, such as up to 2 weeks or more. The flower industry is huge, and flowers are cut and shipped all around the world. The plant medium including the poly-oxygenated metal hydroxide helps the flowers survive during both transport, and after delivery to a customer. A vase can be used by a customer to display the flowers and contain the plant medium. The plant medium can be distributed as a packet by a florist, and the plant medium added to tap water. Considering cut flowers have different survival times, by extending the time flowers remain healthy and beautiful can increase flower sales, and also allow the transportation of flowers that otherwise would not survive the transportation and be marketable to consumers. For instance, unique flowers from remote parts of the earth can't survive multiple flights and extended shipment times to market. Using the plant medium according to this disclosure allows these unique flowers to survive and be marketed globally. The poly-oxygenated metal hydroxide can also help the flowers survive varying and extreme temperatures.

Illustrative Example

On day 0, two like sets of a dozen red roses of were placed in identical vases with the same amount of water on a table proximate each other, and subject to the same ambient conditions. One set was given only the food that came in a typical florist packet, and the other was given the same food that came in the packet, but in addition, one heaping tablespoon of the poly-oxygenated metal hydroxide. These typical florist packets typically contain three ingredients: citric acid, sugar, and bleach. Plants do produce sugar during photosynthesis, but when they're cut, so are their food pipelines. Since flowers can be collected before they've fully developed, they need a little food to bolster their buds. Nothing was added to the water of each vase after day 0.

On day 3, the set of rose flowers with only the food packet showed slight signs of wilting, while the set of rose flowers with the food packet and the poly-oxygenated metal hydroxide looked generally unchanged.

On day 6, the vase of rose flowers with only the food packet showed more signs of wilting, and some rose heads were partially drooped. However, the vase with the set of rose flowers with the food packet and also the poly-oxygenated metal hydroxide showed minimal signs of wilting, and no rose heads were drooping.

On day 9, all but one rose head in the vase with only the food packet were mostly or completely drooping. Noticeably, all the rose heads in the set of flowers with the food packet and the poly-oxygenated metal hydroxide showed only marginal wilting and no drooping rose heads. Also, on day 9, the water in the vase with only the food packet was slightly cloudy, while the water in the vase with the set of flowers with the food packet and the poly-oxygenated metal hydroxide was completely clear. This clear water illustrates that the poly-oxygenated metal hydroxide reduces the decomposition of the cut end of the rose stems, and thus the cut end of the stems are still healthy and able to pass the oxygen gas to the stem to extend the longevity of the rose.

On day 12, all rose heads were completely drooping and expired in the vase with only the food packet. Remarkably, the rose heads were only moderately wilting, with only 1 completely drooping head and a few moderately drooping heads, in the vase with the set of flowers with the food packet and the poly-oxygenated metal hydroxide. Several rose heads still had a straight stem, which is significant for flowers, particularly roses.

Figure 15:
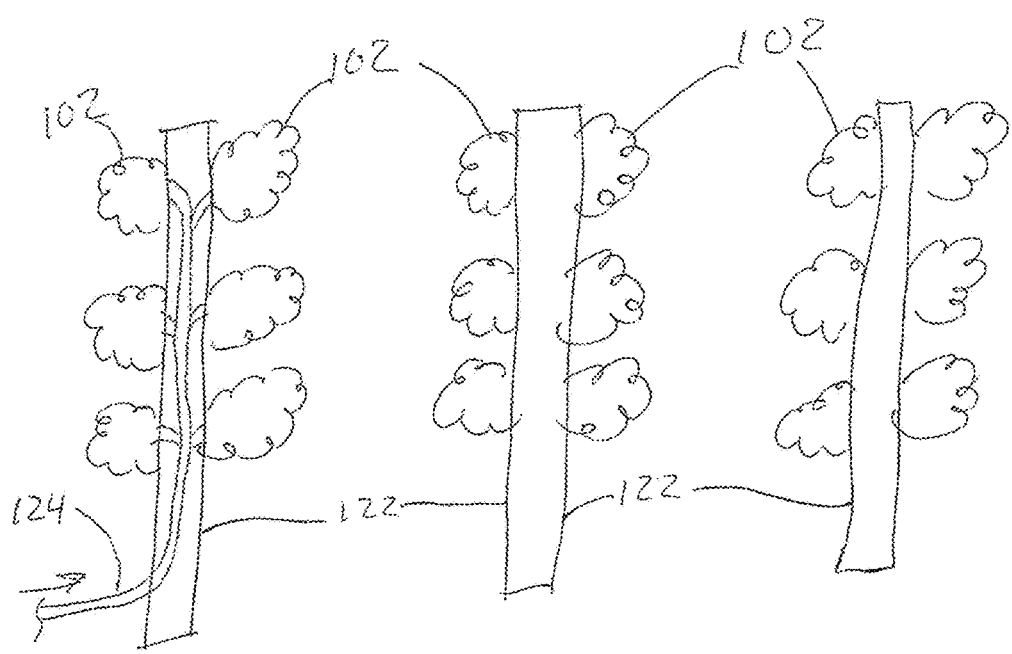
FIG. 15 illustrates vertical farming including plants having a plant medium disposed around the root system of the plant, such as a fluid.

As illustrated in FIG. 15, vertical farming can include the poly-oxygenated metal hydroxide in the plant medium 100 disposed about the roots of the plants 102 where the poly-oxygenated metal hydroxide is fed to the plant roots via a fluid. Each of the plants 102 have their roots supplemented with the plant medium, such as in soil disposed about the roots, or in a nutrient-filled fluid, such as water, communicated via a distribution system and fed to the roots, and a combination thereof. Support ladders or structure 122 support each of the plants 102, where the structure 122 can be used to support a fluid delivery system 124 to distribute the plant medium as a fluid via conduits to the plant roots. The plant medium can comprise of synthetic or organic material. A structure 122 may have holes allowing the plants to grow therethrough, and/or attach thereto, and support the plants. The structure 122 itself may include the poly-oxygenated metal hydroxide, such as being dispersed in the structure. The plant medium can be a slurry or loose paste in some embodiments. One illustrative example of vertical farming is the system of Eden Green of Cleburne, Tex. According to this disclosure, the nutrient-filled water includes the poly-oxygenated metal hydroxide, and the growth time of plants is reduced, which thus increases the yield of the vertical farm per year.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A composition, comprising:
    a plant medium, wherein the plant medium is selected from a group consisting of: soil, dirt, and compost and
    a poly-oxygenated aluminum hydroxide comprising a clathrate containing oxygen gas molecules disposed in the plant medium.

2. The composition as specified in claim 1, wherein the plant medium includes a nutrient.

3. The composition as specified in claim 1, wherein the plant medium comprises soil.

4. The composition as specified in claim 1, wherein the plant medium comprises dirt.

5. The composition as specified in claim 4, wherein the poly-oxygenated aluminum hydroxide is soluble.

6. The composition as specified in claim 5, wherein the poly-oxygenated aluminum hydroxide is soluble and can have a concentration of at least 1 milligram of the poly-oxygenated metal hydroxide to 8 fluid ounces of a fluid.

7. The composition as specified in claim 1, wherein the poly-oxygenated aluminum hydroxide is chlorine-free.

8. The composition as specified in claim 7, wherein the poly-oxygenated aluminum hydroxide comprises particles each having a diameter of less than or equal to 212 μm.

9. The composition as specified in claim 8, wherein the poly-oxygenated aluminum hydroxide is homogeneous.

10. A combination, comprising: a plant; and
    a composition disposed about a portion of the plant, the composition comprising a plant medium, and a poly-oxygenated aluminum hydroxide comprising a clathrate containing oxygen gas molecules,
    wherein the poly-oxygenated aluminum hydroxide composition provides free oxygen for sustaining the life and growth of the plant.

11. The combination as specified in claim 10, further comprising a nutrient.

12. The combination as specified in claim 10, wherein the plant medium comprises soil.

13. The combination as specified in claim 10, wherein the plant medium comprises a fluid.

14. The combination as specified in claim 13, wherein the poly-oxygenated aluminum hydroxide is soluble.

15. The combination as specified in claim 10, wherein the poly-oxygenated aluminum hydroxide is chlorine-free.

16. A method of treating a plant, comprising:
    delivering a poly-oxygenated aluminum hydroxide comprising a clathrate containing oxygen gas molecules to a portion of a plant;
    wherein the poly-oxygenated aluminum hydroxide composition provides free oxygen for sustaining the life and growth of the plant.

17. The method as specified in claim 16, wherein the portion of the plant comprises roots of the plant.

18. The method as specified in claim 16, wherein the composition includes a nutrient.

19. A composition comprising cut flowers having flower stems and cut ends of the flower stems, the cut ends of the flower stems disposed in or enveloped with a plant medium including poly-oxygenated aluminum hydroxide comprising a clathrate containing oxygen gas molecules disposed in the plant medium.

\* \* \* \* \*